United States Patent [19]

Kramer et al.

[11] Patent Number: 5,271,744
[45] Date of Patent: Dec. 21, 1993

[54] SYSTEM AND METHOD FOR RAPID VASCULAR DRUG DELIVERY

[75] Inventors: George C. Kramer, 5 Tiki Cir., Galveston, Tex. 77554; William B. Thomas, Fremont; Jay Wilson, Portola Valley, both of Calif.

[73] Assignee: George C. Kramer, Galveston, Tex.

[21] Appl. No.: 958,279

[22] Filed: Oct. 8, 1992

Related U.S. Application Data

[62] Division of Ser. No. 692,674, Apr. 29, 1991, Pat. No. 5,176,643.

[51] Int. Cl.$^5$ .................... A61M 5/20; A61M 5/315
[52] U.S. Cl. ...................................... 604/51; 604/135
[58] Field of Search ................. 604/49, 51, 28, 135

[56] References Cited

U.S. PATENT DOCUMENTS

| | | |
|---|---|---|
| 3,797,489 | 3/1974 | Sarnoff . |
| 4,445,510 | 5/1984 | Rigby . |
| 4,530,695 | 7/1985 | Phillips et al. . |
| 4,578,064 | 3/1986 | Sarnoff et al. . |
| 4,675,004 | 6/1987 | Hadford . |
| 4,676,781 | 6/1987 | Phillips et al. . |
| 4,710,180 | 3/1988 | Johnson . |
| 4,790,830 | 12/1988 | Hamacher . |
| 4,838,899 | 6/1989 | Massau . |
| 4,850,967 | 7/1989 | Cosmai . |
| 4,894,055 | 1/1990 | Sudnak . |
| 4,969,870 | 11/1990 | Kramer et al. . |
| 5,176,643 | 1/1993 | Kramer et al. .............. 604/135 |

OTHER PUBLICATIONS

Halvorsen, et al., "Evaluation of an Intraosseous Infusion Device for the Resuscitation of Hypovolemic Shock," *The Journal of Trauma*, (Jun. 1990), vol. 30. No. 6, pp. 652-659.

Primary Examiner—Paul J. Hirsch
Attorney, Agent, or Firm—Kevin L. Daffer

[57] ABSTRACT

A device (10) for rapid vascular drug delivery, particularly through the adult sternum or the pediatric tibia, incorporates a cylindrical syringe body (12), fitted with a needle (14). The syringe body is held in a cylindrical main housing (16) having a front barrel (18) with an orifice (20) through which the needle (14) may be extended. A cylindrical actuation handle (22) fits over end (24) of the main housing (16) for sliding movement along the main housing. A syringe plunger (26) contacts drive plunger (28) and extends into the syringe body (12) from end (30) to confine liquid medication (32) in the syringe body (12). A main spring (34) extends between the drive plunger (28) and the actuation handle (22) to bias the actuation handle (22) in its extended position. A needle return spring (38) extends between the front barrel (18) and the syringe body (12) to bias the needle to its retracted position. The drive plunger (28) has an annular peripheral socket (42) for one or more lock balls (44) which engage one or more openings (45) on the main housing (16) to lock the drive plunger in position with respect to the syringe body (12). A mating annular lock ball trip pocket (46) is positioned on inside surface (48) of the actuation handle to allow the device (10) to be fired when the lock ball(s) in socket (42) reach the pocket (46).

5 Claims, 8 Drawing Sheets

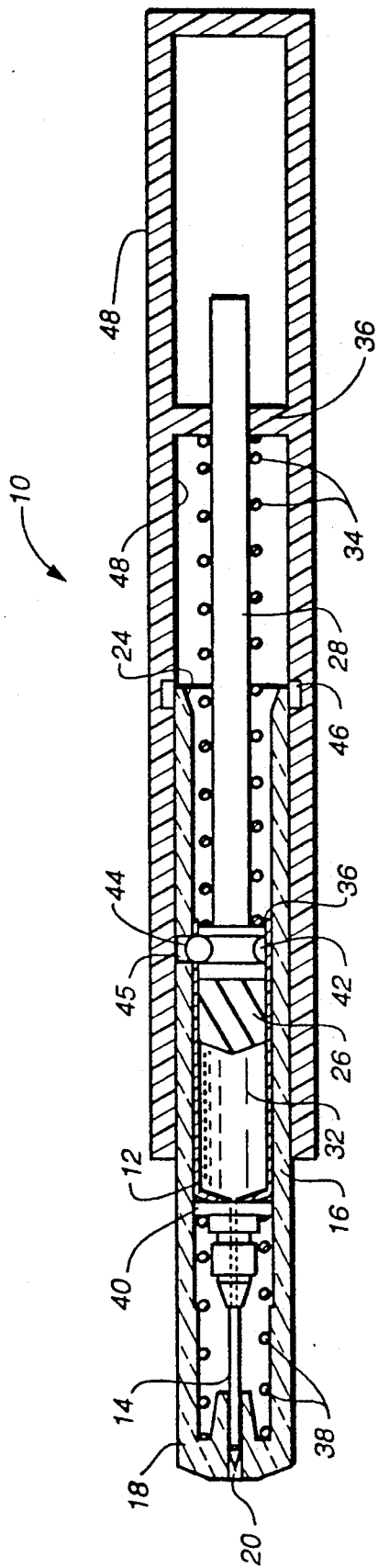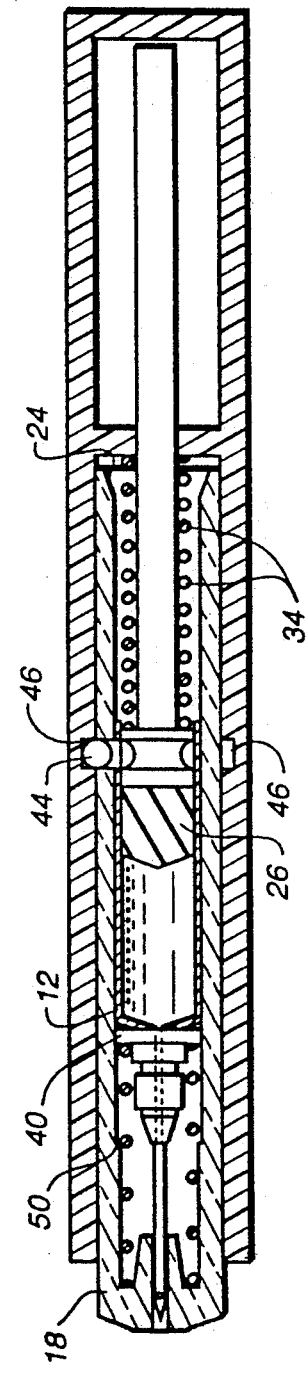
FIG._1
FIG._2

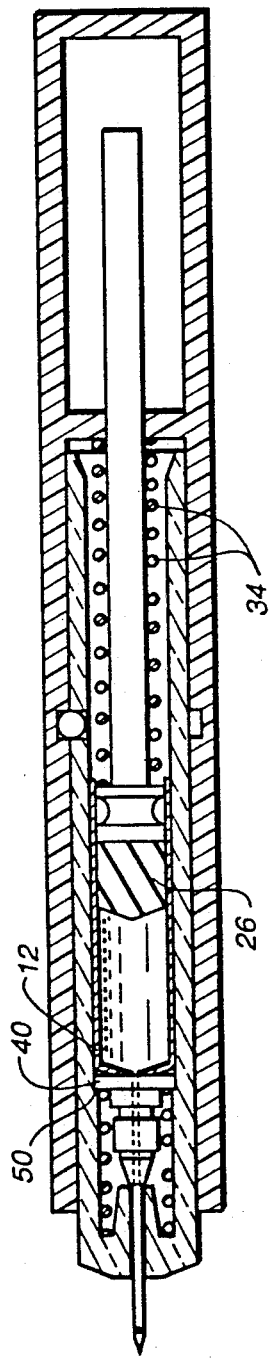
FIG._3
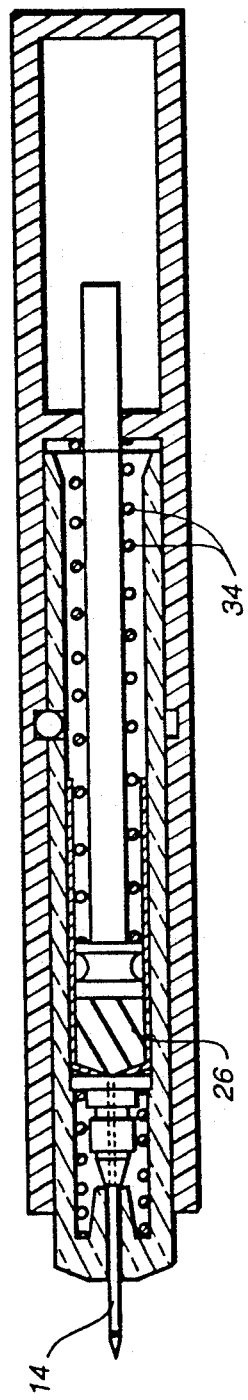
FIG._4
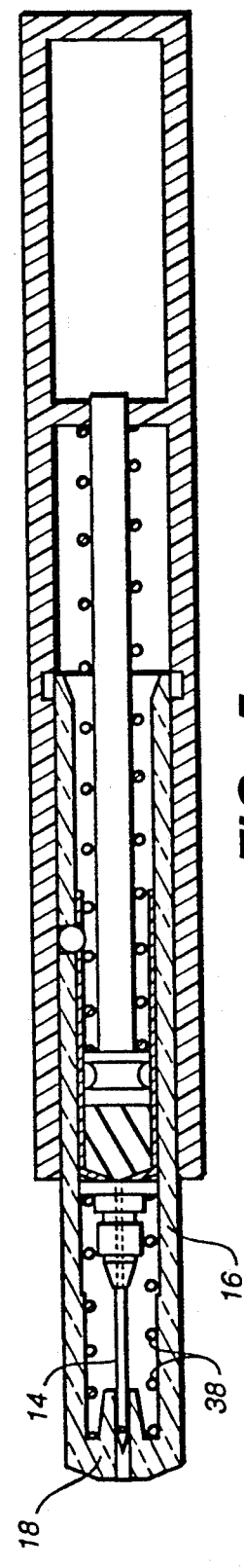
FIG._5

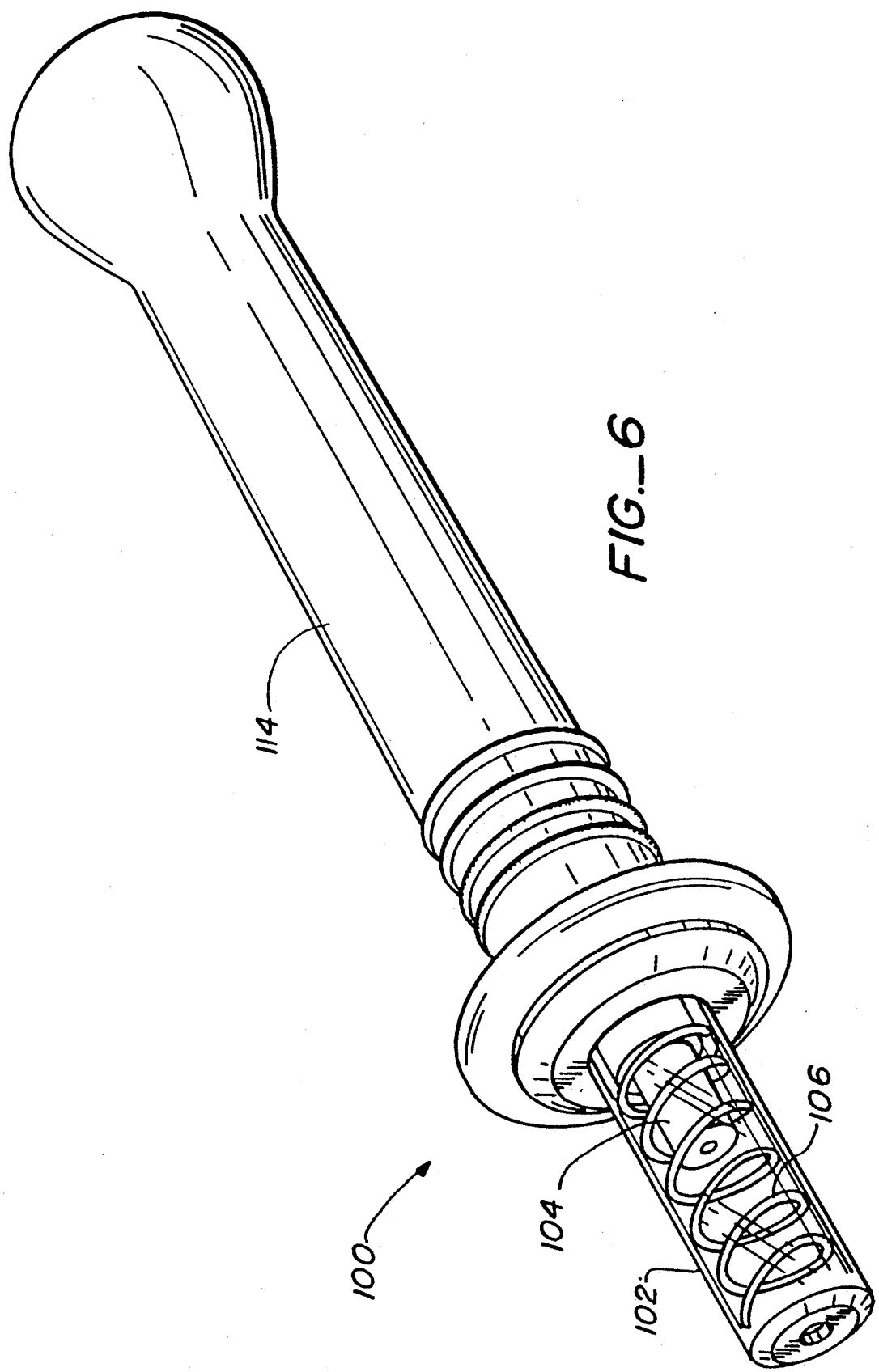

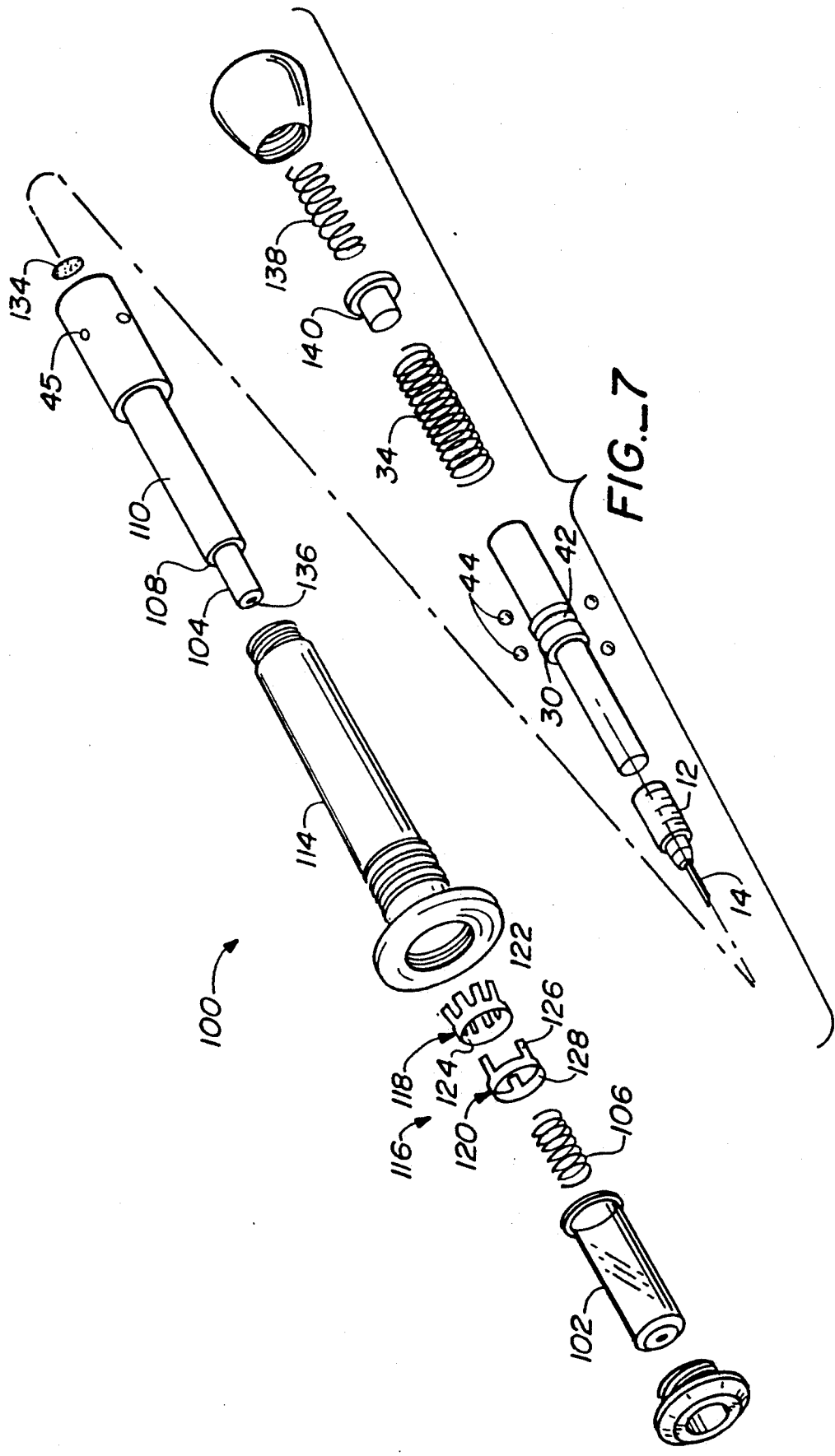

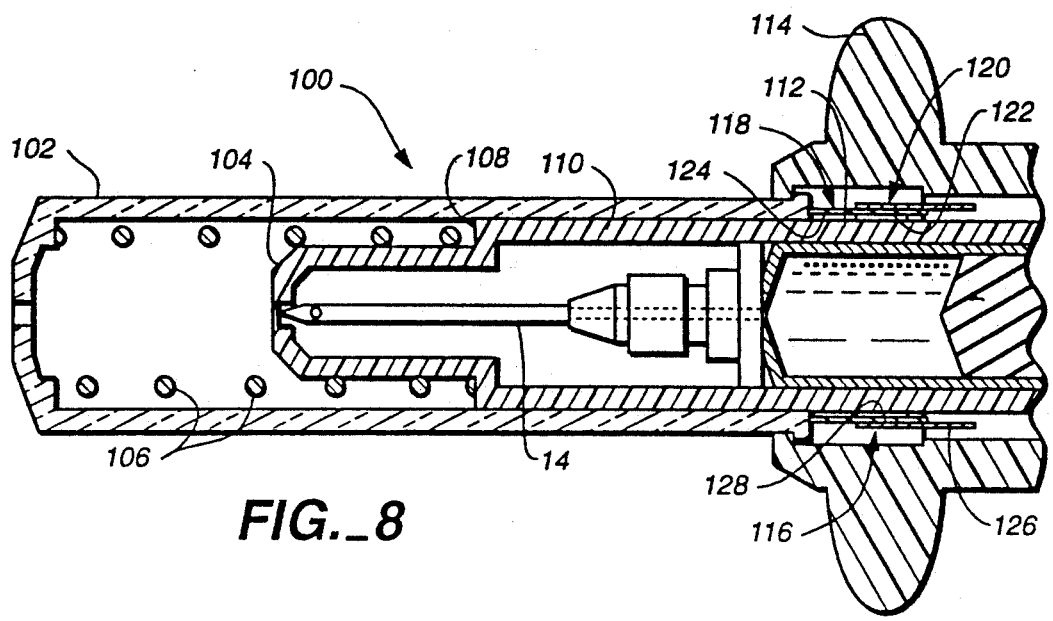
FIG._8
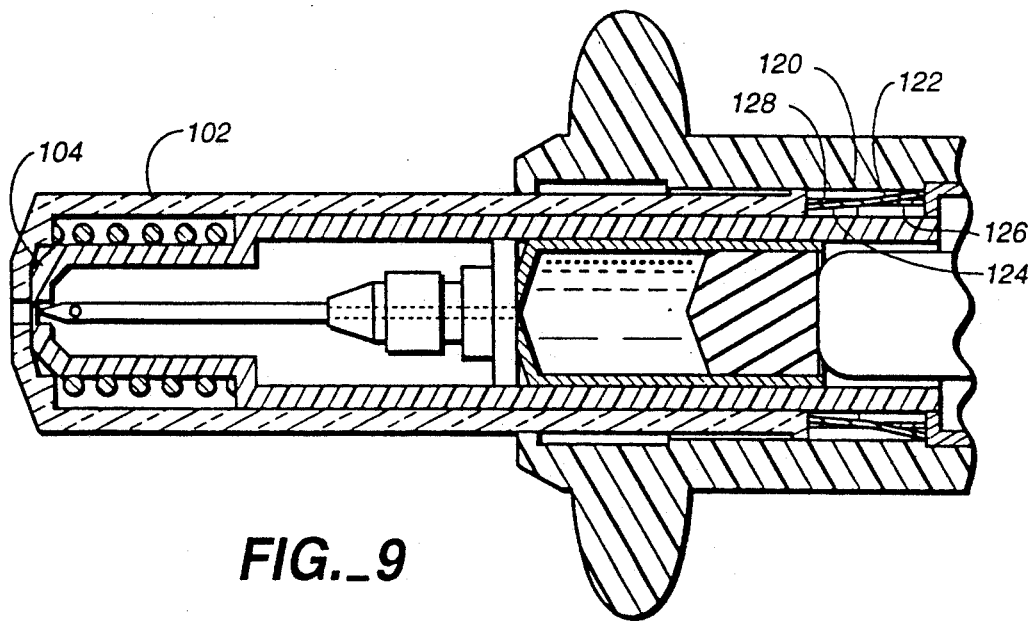
FIG._9

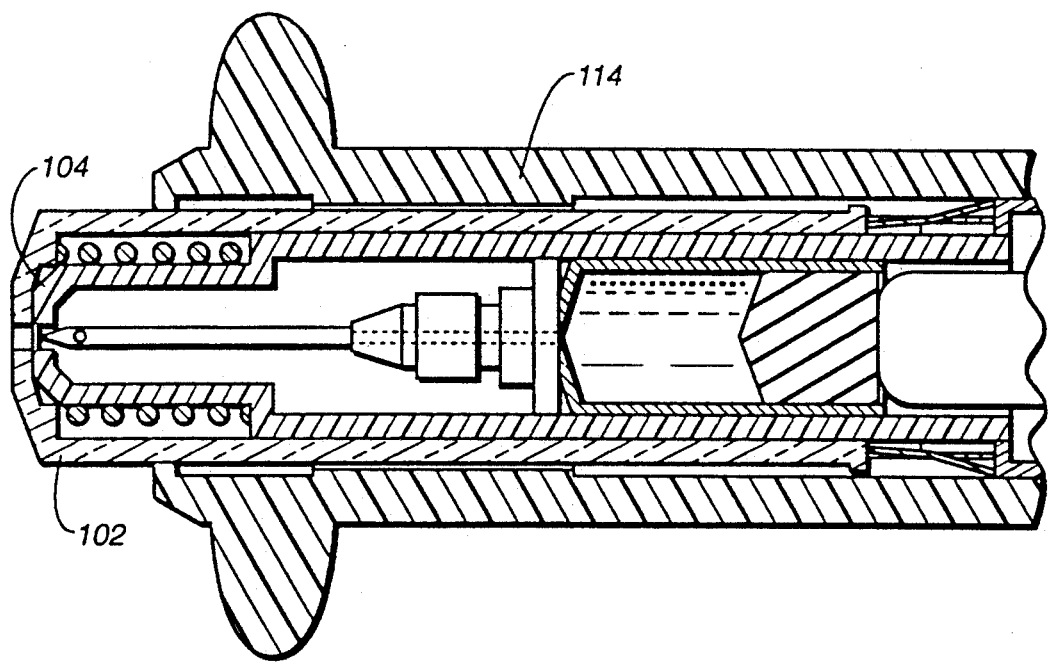
FIG._10

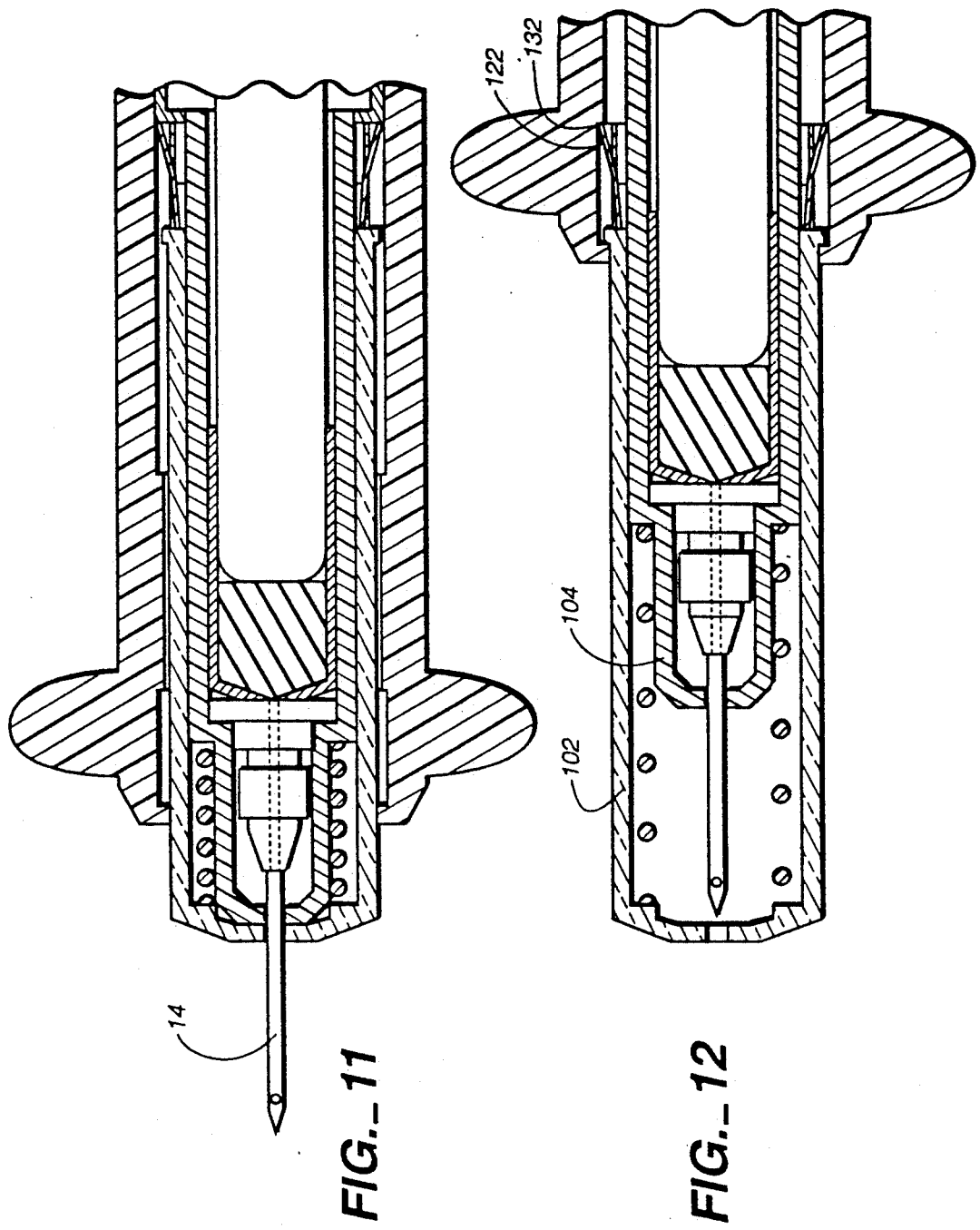

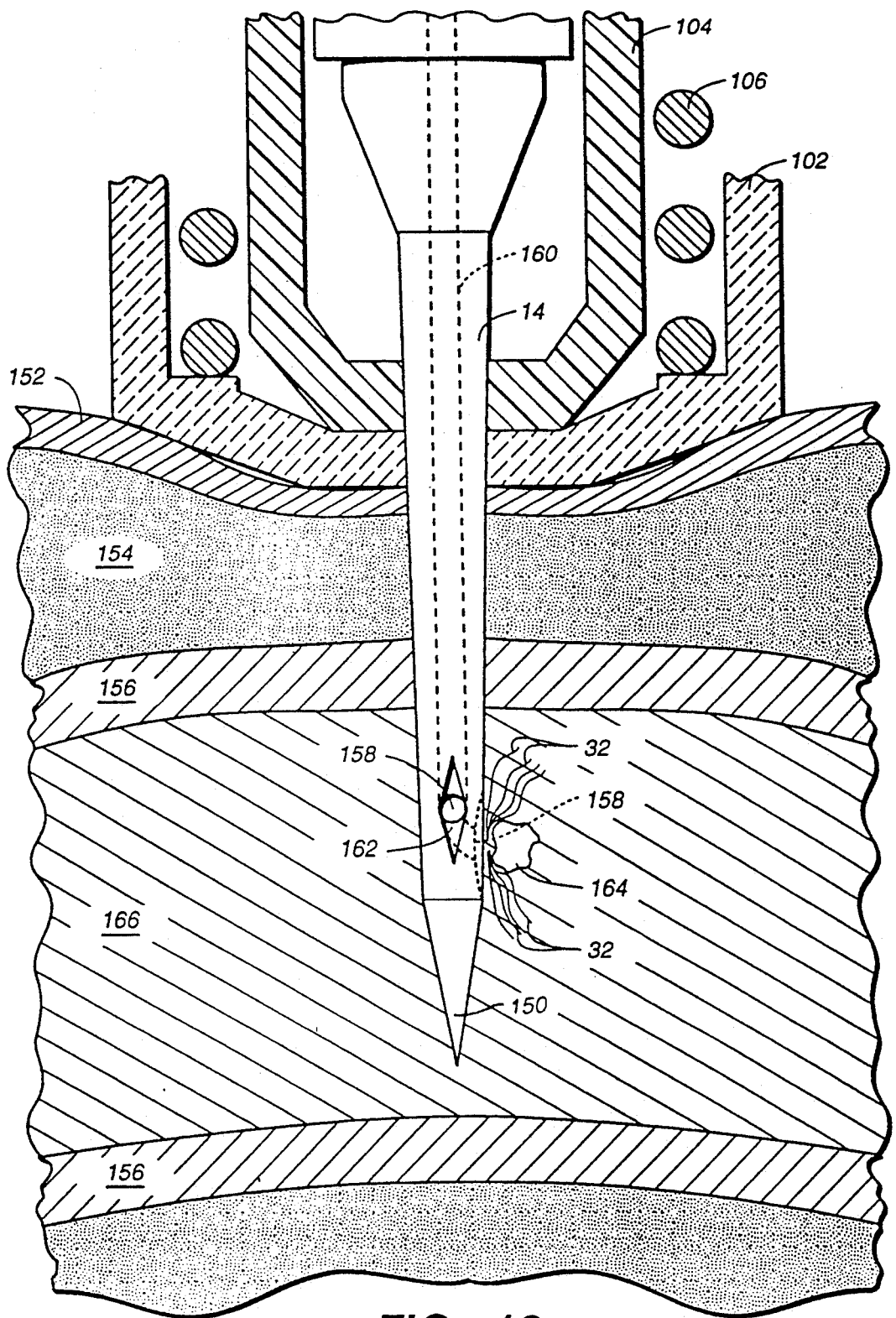
FIG._13

SYSTEM AND METHOD FOR RAPID VASCULAR DRUG DELIVERY

This is a division of application Ser. No. 692,674, filed Apr. 29, 1991, now U.S. Pat. No. 5,176,643.

BACKGROUND OF THE INVENTION

1. Field of the Invention

The present invention relates generally to a system and method for automated, rapid, safe and effective delivery of drugs into the circulatory system. More particularly, it relates to such a system and method in which the drugs are delivered by infusion directly into the red marrow of the adult sternum or the pediatric tibia.

2. Description of the Prior Art

There is a critical need for better and more rapid methods of vascular delivery of drugs. The development of new, life saving drugs and better knowledge of how specific drugs work has established that many drugs can prevent death or reduce morbidity if given in a timely manner. Unfortunately, most drugs need to be infused directly into the blood of the general circulation to be effective, and this is not always easily accomplished. Vascular injections and cannulations are procedures requiring professional skills and training that are usually only possessed by doctors, nurses and paramedics. Even these professionals have a significant failure rate and generate time delays for drug delivery in emergency conditions, when veins are often collapsed due to low blood pressure, and several procedures need to be accomplished as soon as possible. Many other professionals and lay personnel, such as flight attendants, police, life guards and teachers, are trained in advanced first aid and cardiopulmonary resuscitation (CPR), but can not deliver drugs, due to lack of an effective method that does not require more medical training Clearly, there is a need for a simple, better and more rapid means of drug delivery to aid both skilled professionals and para-professionals to expand the utility of life saving drugs.

It has long been known that the red marrow sinuses of bones are virtual non-collapsible veins. Fluids and drugs have been shown to enter the central circulation after intraosseous (IO) infusions as rapidly or even more rapidly than peripheral vein infusions. This IO method can be used to deliver drugs via the long bones of children, but in adults, only the sternum and bones of the pelvic girdle contain large red marrow spaces. Intraosseous infusions are well known and often used in children, but less well utilized in adults. However, most medical emergencies occur in adults.

Many special needles and devices have been made both to sample marrow and to infuse into the red marrow. All of these needles require substantial training and skill for their correct and safe use and take several seconds to minutes to use them properly. Examples of such prior art devices are disclosed in U.S. Pat. Nos. 2,426,535, issued Aug. 26, 1947 to Turkel; 2,773,500, issued Jan. 26, 1955 to Young; 3,750,667, issued Aug. 7, 1973 to Pshenichny et al; 4,969,870, issued Nov. 13, 1990 to Kramer et al., and in the following articles: Tocantins, L. M. and O'Neill, J. F., "Infusion of Blood and Other Fluids into the General Circulation Via the Bone Marrow,", *Surg. Gynecol. Obstet.*, 73, 281-287 (1941); Turkel, H. and Bethell, F. H., "A New and Simple Instrument for Administration of Fluids Through Bone Marrow," *War Medicine*, 5, 222-225 (1944); Glaeser, P. W. and Losek, J. D. "Intraosseous Needles: New and Improved," *Pediat. Emerg. Care*, 4, 135-136 (1989); Sacchetti, A. D., Linkenheimer, R., Lieberman, M., Haviland, P., Kryszozak, L. B., "Intraosseous Drug Administration: Successful Resuscitation from Asystole," *Pediat. Emerg. Care*, 5, 97-98 (1989); Halvorsen, L., Bay, B. K., Perron, P. R. Gunther, R. A., Holcroft, J. W., Blaisdell, F. W., Kramer, G. C., "Evaluation of an Intraosseous Infusion Device for the Resuscitation of Hypovolemic Shock," *J. Traum.*, 30, 652-659 (1990). The above references describe manually inserted needles and techniques which require skill and training for proper use and necessitate many seconds to minutes in use. An automated needle system for delivery of drugs into the red marrow would have great utility.

A variety of auto-injection syringes for intramuscular or subcutaneous injections are also known in the art. Examples of such syringes are disclosed in the following U.S. Pat. Nos.: 3,396,726, issued Aug. 13, 1968 to Sarnoff; 3,712,301, issued Jan. 23, 1973 to Sarnoff; 3,882,863, issued May 13, 1975 to Sarnoff et al.; 4,031,893, issued Jun. 28, 1977 to Kaplan et al. However, these syringes are not designed, nor could they be effectively or safely used for injecting into the red marrow sinuses of bones, nor do they prevent needles used in the procedures from being exposed so that there is a danger of accidental needle punctures in use of these syringes.

SUMMARY OF THE INVENTION

Accordingly, it is an object of this invention to provide a device and method for very rapid, automated and safe infusions of fluid and drugs in the circulatory system, e.g., into red marrow.

It is another object of the invention to provide such a device and method which will automatically puncture a bone containing the red marrow, place a needle into the red marrow, and infuse fluid into the circulatory system via the red marrow.

It is a further object of the invention to provide such a device and method which automatically covers the needle before and after use to prevent accidental needle punctures.

It is a still further object of the invention to provide such a device and method which can be used either with the adult sternum or the pediatric tibia.

It is yet another object of the invention to provide such a device and method that compresses the skin over the bone in use to reduce the anatomical variability of skin thickness.

It is yet a further object of the invention to provide such a device and method that imparts velocity to a needle and syringe component such that momentum rapidly places the needle through the skin and bone and into the marrow.

It is still another object of the invention to provide a needle which is adapted for use with such a device and method.

It is a still further object of the invention to provide such a needle which facilitates drug delivery into the marrow, yet prevents back flow of fluid out of the bone.

The attainment of these and related objects may be achieved through use of the novel device and method for rapid vascular drug delivery herein disclosed. In a first aspect of the invention, a device for rapid drug delivery in accordance with this invention has a main housing with a front end. There is a forward directed aperture on the front end of the main housing. A syringe body has a front end and a rear end. The syringe body is slideably positioned in the main housing. A needle has a central bore communicating with at least one opening proximate to a tip of the needle. The needle is attached to the front end of the syringe body, communicates with an interior of said syringe body and is positioned to extend through the aperture of the main housing. A drive plunger extends from the rear end of the syringe body. A means on the main housing and engaging the drive plunger locks and unlocks the drive plunger in position at the rear end of the syringe body. A means is connected to the drive plunger for applying propelling force to the drive plunger to move the syringe body along the main housing in a first direction to extend the needle from the aperture when the device is pressed against a patient and to expel the drug from the syringe body into the patient. A means is connected to the syringe body to move the syringe body in a second direction opposite to the first direction for withdrawing the needle into the aperture when the device is no longer pressed against a patient.

In a second aspect of the invention, a device for delivery of a drug in liquid form to red marrow has a main housing with a front end. There is a forward directed aperture on the front end of the main housing. A syringe body has a front end and a rear end. The syringe body is slideably positioned in the main housing. A needle having a central bore communicating with at least one opening proximate to a tip of the needle is attached to the front end of the syringe body, communicates with an interior of said syringe body and is positioned to extend through the aperture of the main housing an appropriate distance for passing through a patient's skin, penetrating a bone and entering the red marrow inside the bone. A means imparts a force to the syringe body and the needle to extend the needle through the aperture of the main housing the appropriate distance at a sufficient velocity to pass through the patient's skin, penetrate the bone and enter the red marrow. A means discharges the drug in liquid form from the syringe, through the needle and into the red marrow.

In a third aspect of the invention, a needle for use in a device for delivery of a drug in liquid form has a body with a taper along its length and a conical, orifice free tip. A central bore communicates with a plurality of orifices proximate to the tip. The plurality of orifices are positioned circumferentially on the needle at different distances from the tip.

In a fourth aspect of the invention, a method for delivering a drug in liquid form to red marrow includes positioning a syringe including a needle above a patient's skin at a location over a bone containing red marrow. Sufficient velocity is imparted to the syringe so that said needle will have sufficient momentum to pass through the patient's skin, penetrate the bone and enter the red marrow. The drug in liquid form is discharged from the syringe, through the needle and into the red marrow.

The attainment of the foregoing and related objects, advantages and features of the invention should be more readily apparent to those skilled in the art, after review of the following more detailed description of the invention, taken together with the drawings, in which:

BRIEF DESCRIPTION OF THE DRAWINGS

FIG. 1 is a cross-section view of a first embodiment of a device for rapid vascular drug delivery of the invention.

FIGS. 2-5 are similar cross-section views of the device of FIG. 1 at different stages in its use.

FIG. 6 is an external perspective view of a second embodiment of a device for rapid vascular drug delivery of the invention.

FIG. 7 is an exploded perspective view of the device of FIG. 6.

FIGS. 8-12 are cross-section views of a portion the device of FIGS. 6-7.

FIG. 13 is an enlarged side view of a portion of the devices of FIGS. 1-12 in use.

DETAILED DESCRIPTION OF THE INVENTION

Turning now to the drawings, more particularly to FIG. 1, there is shown a device 10 for rapid vascular drug delivery, particularly through the adult sternum or the pediatric tibia. The device 10 incorporates a cylindrical syringe body 12, fitted with a double side-holed pencil point needle 14. The syringe body is held in a cylindrical main housing 16 having a front barrel 18 with an orifice 20 through which the needle 14 may be extended. A cylindrical actuation handle 22 fits over end 24 of the main housing 16 for sliding movement along the main housing. A syringe plunger 26 contacts drive plunger 28 and extends into the syringe body 12 to confine liquid medication 32 in the syringe body 12. A main spring 34 extends between the drive plunger 28 and partition 36 on the actuation handle 22 to bias the actuation handle 22 in its extended position along the main housing 16 as shown in FIG. 1. A needle return spring 38 extends between the front barrel 18 and a collar 40 on the syringe body 12 to bias the needle to its retracted position as shown in FIG. 1. The main spring 34 exerts a stronger biasing force when compressed than the needle return spring 38. The drive plunger 28 has an annular peripheral socket 42 for one or more lock balls 44, which engage one or more openings 45 on the main housing 16 to lock the drive plunger in position with respect to the syringe body 12. A mating annular lock ball trip pocket 46 is positioned on inside surface 48 of the actuation handle to allow the device 10 to be fired when the lock ball(s) in socket 42 reach the pocket 46. In FIG. 1, the device 10 is shown in its uncocked position.

In use, the device 10 is placed with the end of the front barrel 18 on the midline of the sternum at the second or third intercostal space, and then the device 10 is pushed against the sternum. Compression of the spring 34 behind the syringe body 12 occurs as the front barrel 18 is pushed toward the actuation handle 22 and generates a force that will be used for needle 14 advancement and drug 32 injection. When an adequate force has been stored in the spring 34, the front barrel 18 has been pushed back to a point so that the lock ball(s) 44 are able to enter the trip pocket 46, as shown in FIG. 2. This entry releases the lock ball(s) 44, so that the main spring 34 is free to drive the syringe body 12 and the needle 14 forward with a force of about 25 to about 40 pounds until collar 40 rests against ridge 50, as shown in FIG. 3. The needle 14 is extended from about 8 mm to about 16 mm in order to insure that side holes in the needle are in the red marrow. The main spring 34 then pushes the syringe plunger 26 forward to the position shown in FIG. 4 to deliver the drug 32 through the extended needle 14 to the red marrow in the sternum. Needle placement takes about 1/10th of a second, while drug delivery usually occurs in less than a second. Operation in this manner causes the syringe body 12 to reach a sufficient velocity so that the penetration of the needle 14 into the red marrow occurs in a single, rapid, uninterrupted motion due to momentum of the syringe body 12 and needle 14. Relying on momentum in this manner means that a smaller diameter needle can be used than would be required if the penetration resulted from application of penetrating force on the needle while it was at rest against the skin or bone. Upon completion of drug delivery, the operator releases the pressure against the sternum, and the needle retraction spring 38 withdraws the needle 14 into the barrel 18 of the main housing 16 to the position shown in FIG. 5.

FIGS. 6-12 show another device 100 for the rapid delivery of a drug to the red marrow. The device 100 incorporates a locking, cylindrical protective cover 102 over front barrel 104 to insure that needle 14 is never exposed except when the device 100 is both pressed against the patient's body and actuated. A cover return spring 106 is positioned between the protective cover 102 and shoulder 108 on cylindrical main housing 110 of the device. The protective cover 102 has an end 112 that extends into actuation handle 114 of the device 100. End 112 is equipped with a tab locking mechanism 116 that, once actuated, prevents the protective cover 102 from being moved from its extended position as shown in FIG. 8 to its withdrawn position, against the barrel 104, as shown in FIG. 9. The locking mechanism 116 consists of two parts: a lock 118 circumferentially positioned around the end 112 between the protective cover 102 and the actuation handle 114, and a sleeve 120 concentrically positioned over the lock 118. The lock 118 has a plurality of spring tabs 122 extending rearward of the actuation handle 114 from a cylindrical base 124. The sleeve 120 has a plurality of projections 126, which are not springs, extending rearward beyond the tabs 122 from a similar cylindrical base 128. With the parts of the device 100 in the positions shown in FIG. 8, prior to use of the device 100, the cylindrical base 128 of the sleeve 120 rests over the spring fingers 122 of the lock 118, holding them down. A sealing membrane 134 is provided inside the barrel 104, over orifice 136, to protect the needle 14 prior to use of the device.

In use of the device 100, with the spring fingers 122 in their down position, the protective cover 102 is free to retract against the barrel 104 to the position shown in FIG. 9, when the protective cover 102 is pressed downward against, e.g., the adult sternum or the pediatric tibia. As the protective cover 102 moves toward the barrel 104, the projections 126 of the sleeve 120 engage shoulder 130 of the actuating handle 114, so that the base 128 of the sleeve 120 is pushed down over the base 124 of the lock 118, allowing the spring fingers 122 of the lock 118 to spring outward, as shown in FIG. 9. Continued downward pressure of the device 100 on the adult sternum or pediatric tibia moves the protective cover 102 and the barrel 104 into the actuating handle 114, as shown in FIG. 10, until the main body 108 and the actuating handle reach the firing position, as in the FIGS. 1-5 embodiment. At that time, firing occurs, the needle 14 is extended into the sternum or tibia, and the drug is ejected into the red marrow through the needle 14, as shown in FIG. 11 in the same manner as in the FIGS. 1-5 embodiment. When the device 100 is no longer pressed against the patient, the protective cover 102 is returned to its original position by the force of spring 106, as shown in FIG. 12. Because the spring tabs 122 have sprung outward, they engage shoulder 132, forward of the shoulder 130 on the actuating handle, to lock the protective cover 102 over the needle 14. Thus, the needle is never exposed except when the device 100 is actually pressed against the patient, and the needle 14 cannot be re-exposed after actuation, even if the device is again pressed against the patient or any object. In addition to the main spring 34, a secondary spring 138, separated from the main spring by member 140, is provided to ensure that there is still a spring force urging the needle 14 forward when it is fully extended. Except as shown and described, the construction and operation of the FIGS. 6-10 embodiment of the invention is the same as that of the FIGS. 1-5 embodiment.

FIG. 13 shows details of the needle 14 used in the devices 10 and 100. The needle 14 has a slight taper along its length toward a conical, orifice free tip 150. The taper promotes a good seal between the needle 14 and bone 156. The tip 150 of the needle 14 is free of an orifice because orifices located there would tend to clog during penetration of the bone 156. Orifices 158 are located behind the conical tip 150 and communicate with a central bore 160 extending the length of the needle 14 to communicate with the reservoir of drug 32 (FIG. 1). The orifices 158 are staggered around the circumference of the needle 14 and connect to slits 162 extending vertically along the side of the needle. This configuration and placement of the orifices 158 and the slits 162 allow discharge of the drug 32 from an orifice 158, even if it is partially blocked by a tissue globule 164 in the red marrow 166.

Examples of drugs that can be life saving for specific medical emergencies if administered into the central circulation in a timely manner, and hence, candidates for packaging in the devices 10 and 100, are shown in the following table:

| Drug | Medical Emergency |
| --- | --- |
| Epinephrine or related compounds | Cardiac arrest; Anaphylactic shock |
| Naloxone | Narcotic overdose |
| Atropine sulfate | Organophosphate poisoning |
| Benadryl | Anaphylactic shock |
| TPA (tissue plasminogen activator) | Myocardial infarction |
| Valium | Convulsion/seizures |
| Sodium pentobarbital | Convulsion/seizures |
| Lidocaine | Cardiac arrhythmias |

All of the above medical emergencies are and can be life threatening. The vascular delivery of the above drugs can be life saving. Even a few seconds delay in therapy can be a matter of life or death in the above emergencies. The described invention can administer these drugs into the central circulation, often in less than 1 or 2 seconds, can be safely and effectively performed by a lay person with minimal training and, overall, offers a safe, effective, automated and extremely rapid means to treat medical emergencies.

Because momentum is used to advance the needle through the cortical bone and into the red marrow, even a small gauge needle, such as a 20 to 25 gauge simple pencil point with multiple sideholes could be properly placed. Because the effective dose of most of the previously listed drugs could be carried in exceedingly small volumes, such as 0.1 to 0.2 ml or less, such a small gauged needle could be used for rapid drug delivery. Alternatively, a larger needle (12 to 18 gauge), either a simple pencil point or the design previously described could be used to administer rapidly 1.0 to 5.0 ml of fluid. The invention and these needles and drugs can be delivered effectively into circulation in as short a time as 1 to 2 seconds or less.

While the invention has been shown in two preferred forms, various modifications of it could be made. For example, the device could be constructed so that it is cocked or loaded prior to placing it in contact with the patient, and merely fired after it is pressed against the patient with a suitable pressure. The devices 10 and 100 have been shown and described as configured for IO infusion. The same principle of an automatic syringe that is automatically spring loaded for injection by pressing against the patient could be adapted to an automatic syringe for subcutaneous or intramuscular injection as well.

It should now be readily apparent to those skilled in the art that a device and method for automated, safe and effective delivery of drugs into the circulatory system has been provided. The device and method automatically punctures a bone containing red marrow, places a needle into the red marrow, and infuses fluid into the circulatory system via the red marrow. The device and method automatically covers the needle before and after use to prevent accidental needle punctures. The device and method can be used either with the adult sternum or the pediatric tibia. The needle of the device is specially adapted for use with such a device and method.

It should further be apparent to those skilled in the art that various changes in form and details of the invention as shown and described may be made. It is intended that such changes be included within the spirit and scope of the claims appended hereto.

What is claimed is:

1. A method for delivering a drug in liquid form to marrow, which comprises positioning a syringe including a needle above a patient's skin at a location over a bone containing marrow, releasibly extending said needle from said syringe with sufficient momentum to pass through the patient's skin, penetrate the bone and enter said marrow, and discharging the drug in liquid form from the syringe, through the needle and into said marrow.

2. The method for delivering a drug in liquid form to marrow of claim 1 in which said marrow is located in an sternum.

3. The method for delivering a drug in liquid form to marrow of claim 1 in which said marrow is located in a tibia.

4. A method for delivery of a drug in liquid form by injection, which comprises positioning a syringe including a needle in a housing above a patient's skin, applying a spring load to said syringe by pressing the housing against the patient, releasing the spring load to extend said needle with velocity sufficient to penetrate bone prior to and during penetration of the patient's skin, injecting the drug through the needle, and withdrawing the needle from the patient into the housing.

5. The method for delivery of a drug in liquid form by injection of claim 4, wherein said velocity is sufficient such that a tip of the needle penetrates a bone and enters marrow within the bone.

* * * * *